(12) United States Patent
Blain et al.

(10) Patent No.: US 11,351,038 B2
(45) Date of Patent: Jun. 7, 2022

(54) INTERBODY FUSION DEVICE

(71) Applicant: Spinal Elements, Inc., Carlsbad, CA (US)

(72) Inventors: Jason Blain, Encinitas, CA (US); Dean Johnson, Solana Beach, CA (US)

(73) Assignee: Spinal Elements, inc., Carlsbad, CA (US)

( * ) Notice: Subject to any disclaimer, the term of this patent is extended or adjusted under 35 U.S.C. 154(b) by 114 days.

(21) Appl. No.: 16/867,279

(22) Filed: May 5, 2020

(65) Prior Publication Data

US 2020/0330241 A1 Oct. 22, 2020

Related U.S. Application Data

(60) Continuation of application No. 15/665,774, filed on Aug. 1, 2017, now Pat. No. 10,675,156, which is a division of application No. 13/768,922, filed on Feb. 15, 2013, now Pat. No. 9,750,616.

(60) Provisional application No. 61/600,435, filed on Feb. 17, 2012.

(51) Int. Cl.
*A61F 2/44* (2006.01)
*A61B 17/86* (2006.01)
*A61F 2/46* (2006.01)
*A61F 2/30* (2006.01)

(52) U.S. Cl.
CPC .......... *A61F 2/4455* (2013.01); *A61B 17/869* (2013.01); *A61F 2/4611* (2013.01); *A61F 2002/30289* (2013.01); *A61F 2002/30578* (2013.01); *A61F 2002/30593* (2013.01); *A61F 2002/30787* (2013.01); *A61F 2002/30904* (2013.01)

(58) Field of Classification Search
CPC ..... A61B 17/869; A61B 17/8052–8057; A61F 2002/30578; A61F 2002/30904; A61F 2002/30289; A61F 2002/30787; A61F 2002/4475; A61F 2/445; A61F 2/4611
USPC ........ 606/104, 301–321, 213, 218, 232–233, 606/151; 411/425, 438, 456, 451.3; 607/131; 623/17.16
See application file for complete search history.

(56) References Cited

U.S. PATENT DOCUMENTS

| 5,055,104 | A | 8/1991 | Ray |
| 5,263,953 | A | 11/1993 | Bagby |
| 5,489,307 | A | 2/1996 | Kuslich et al. |
| 5,662,683 | A | 9/1997 | Kay |
| 5,824,008 | A | 10/1998 | Bolduc et al. |
| 5,885,299 | A | 3/1999 | Winslow et al. |

(Continued)

FOREIGN PATENT DOCUMENTS

| WO | WO 2010/111802 | 10/2010 |
| WO | WO 2017/175024 | 10/2017 |

OTHER PUBLICATIONS

Invitation to Pay Additional Search Fees in International Application No. PCT/US2020/031581, dated Aug. 4, 2020.

(Continued)

*Primary Examiner* — Marcela I. Shirsat
(74) *Attorney, Agent, or Firm* — Knobbe, Martens, Olson & Bear, LLP

(57) ABSTRACT

Devices for fixing interbody fusion devices to bone by helically or corkscrew-shaped elements are provided. Methods for surgically implanting an interbody fusion device using helically-shaped fixation wire are provided.

20 Claims, 16 Drawing Sheets

(56) References Cited

U.S. PATENT DOCUMENTS

| | | |
|---|---|---|
| 6,056,749 A | 5/2000 | Kuslich |
| 6,066,175 A | 5/2000 | Henderson et al. |
| 6,113,637 A | 9/2000 | Gill et al. |
| 6,156,037 A | 12/2000 | Le Huec et al. |
| 6,231,610 B1 | 5/2001 | Geisler |
| 6,276,883 B1 | 8/2001 | Unsworth et al. |
| 6,296,656 B1 | 10/2001 | Bolduc et al. |
| 6,432,106 B1 | 8/2002 | Fraser |
| 6,551,319 B2 | 4/2003 | Lieberman |
| 6,551,322 B1 | 4/2003 | Lieberman |
| 6,730,127 B2 | 5/2004 | Michelson |
| 6,896,676 B2 | 5/2005 | Zubok et al. |
| 6,953,462 B2 | 10/2005 | Lieberman |
| 6,984,234 B2 | 1/2006 | Bray |
| D524,443 S | 6/2006 | Blain |
| 7,056,341 B2 | 6/2006 | Crozet |
| 7,077,864 B2 | 7/2006 | Byrd, III et al. |
| 7,094,239 B1 | 8/2006 | Michelson |
| 7,112,222 B2 | 9/2006 | Fraser et al. |
| D533,277 S | 12/2006 | Blain |
| 7,172,627 B2 | 2/2007 | Fiere et al. |
| D539,934 S | 4/2007 | Blain |
| D541,940 S | 5/2007 | Blain |
| 7,601,167 B2 | 10/2009 | Liberman |
| 7,766,947 B2 | 8/2010 | Hawkes et al. |
| 7,850,731 B2 | 12/2010 | Brittan et al. |
| 7,935,123 B2 | 5/2011 | Fanger et al. |
| 8,100,955 B2 | 1/2012 | Blain et al. |
| 8,142,504 B2 | 3/2012 | Petit |
| 8,333,804 B1 | 12/2012 | Wensel |
| 8,394,107 B2 | 3/2013 | Fanger et al. |
| 8,500,811 B2 | 8/2013 | Blain et al. |
| 8,523,945 B1 | 9/2013 | Wensel |
| 8,740,983 B1 | 6/2014 | Arnold et al. |
| 8,801,785 B2 | 8/2014 | Brittan et al. |
| 8,808,304 B2 | 8/2014 | Weiman et al. |
| 8,840,668 B1 | 9/2014 | Donahoe et al. |
| 8,900,310 B2 | 12/2014 | Carlson et al. |
| 8,926,702 B2 | 1/2015 | Gorek et al. |
| 8,945,227 B2 | 2/2015 | Kirschman |
| 9,180,022 B2 | 11/2015 | Georges et al. |
| 9,375,237 B2 | 6/2016 | Keegan et al. |
| 9,427,330 B2 | 8/2016 | Pertersheim et al. |
| 9,750,616 B2 | 9/2017 | Blain et al. |
| 10,238,439 B2 | 3/2019 | Prybis et al. |
| 10,342,678 B2 | 7/2019 | Flores et al. |
| 10,675,156 B2 | 6/2020 | Blain et al. |
| 2002/0022845 A1 | 2/2002 | Zdeblick et al. |
| 2004/0193269 A1 | 9/2004 | Fraser et al. |
| 2004/0254579 A1 | 12/2004 | Buhren et al. |
| 2004/0258502 A1 | 12/2004 | Unsworth et al. |
| 2005/0049593 A1 | 3/2005 | Duong et al. |
| 2005/0143733 A1 | 6/2005 | Petit |
| 2006/0201289 A1 | 9/2006 | Davidson et al. |
| 2008/0294262 A1 | 1/2008 | Levieux |
| 2008/0140203 A1 | 6/2008 | Davis |
| 2008/0161925 A1 | 7/2008 | Brittan et al. |
| 2008/0300634 A1 | 12/2008 | Gray |
| 2009/0012529 A1 | 1/2009 | Blain et al. |
| 2009/0018592 A1 | 1/2009 | Pitbladdo |
| 2009/0030520 A1 | 1/2009 | Biedermann et al. |
| 2009/0275988 A1 | 11/2009 | Baynham |
| 2010/0228297 A1 | 9/2010 | Bray et al. |
| 2010/0256690 A1* | 10/2010 | Appenzeller ........ A61B 17/869 606/305 |
| 2010/0305704 A1 | 12/2010 | Messerli |
| 2011/0166660 A1 | 7/2011 | Laurence |
| 2011/0190892 A1 | 8/2011 | Man |
| 2011/0230918 A1 | 9/2011 | Gorek et al. |
| 2012/0232597 A1* | 9/2012 | Saidha ................. A61B 17/869 606/305 |
| 2013/0060337 A1 | 3/2013 | Petersheim et al. |
| 2013/0079879 A1 | 3/2013 | Suh |
| 2013/0190874 A1 | 7/2013 | Glazer |
| 2013/0218277 A1 | 8/2013 | Blain et al. |
| 2013/0268008 A1 | 10/2013 | McDonough et al. |
| 2016/0220388 A1 | 8/2016 | Flores et al. |
| 2016/0296341 A1 | 10/2016 | Tatsumi |
| 2017/0224389 A1 | 8/2017 | Tatsumi |
| 2019/0083270 A1 | 3/2019 | Milz et al. |
| 2019/0307579 A1 | 10/2019 | Flores et al. |
| 2020/0352739 A1 | 11/2020 | Ouidja et al. |

OTHER PUBLICATIONS

International Search Report and Written Opinion in International Application No. PCT/US2020/031581, dated Oct. 14, 2020.

International Preliminary Report on Patentability and Written Opinion in International Application No. PCT/US2020/031581, dated Nov. 18, 2021.

* cited by examiner

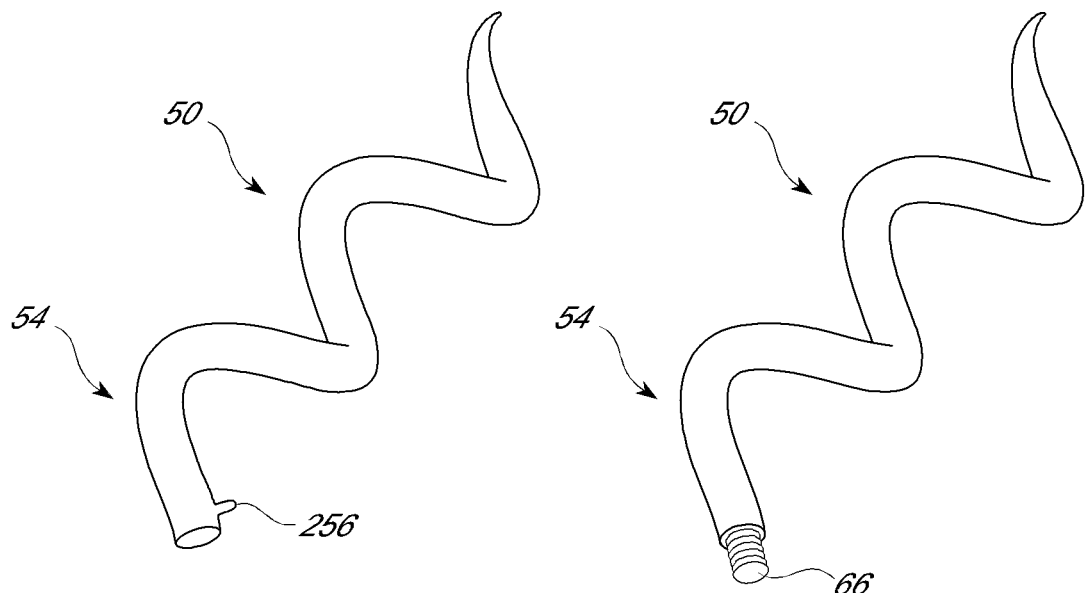
FIG. 12A
FIG. 12C
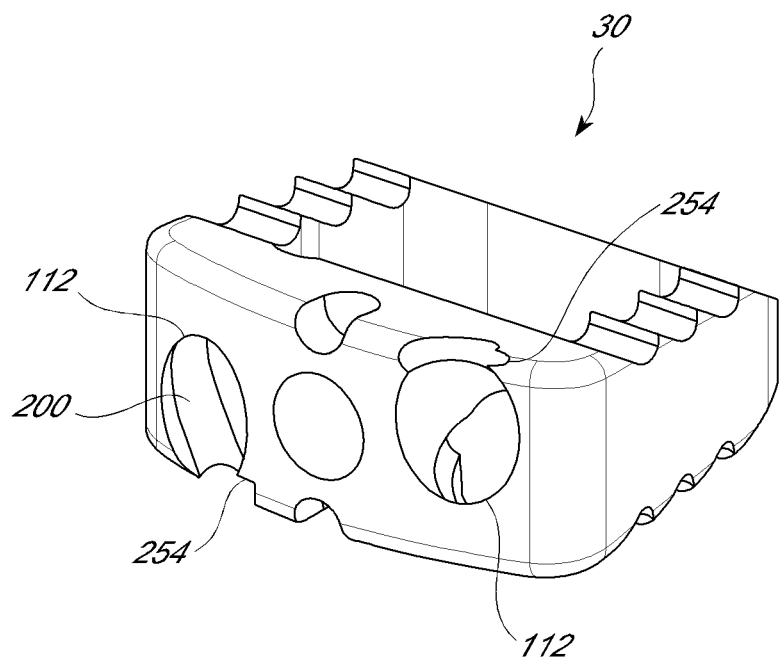
FIG. 12B

INTERBODY FUSION DEVICE

RELATED APPLICATION INFORMATION

This application is a continuation of U.S. application Ser. No. 15/665,774, filed Aug. 1, 2017, which is a divisional of U.S. application Ser. No. 13/768,922, filed Feb. 15, 2013, which claims priority under 35 U.S.C. § 119(e) to U.S. Provisional Patent Application No. 61/600,435, filed Feb. 17, 2012, the disclosure of each is incorporated by reference herein in its entirety.

BACKGROUND OF THE INVENTION

Field of the Invention

This invention relates generally to systems and methods for performing spinal fixation and, in particular, to interbody spacer devices.

Description of the Related Art

Advancing age, as well as injury, can lead to degenerative changes in the bones, discs, joints and ligaments of the spine, producing pain and instability. Under certain circumstances, alleviation of the problems can be provided by performing spinal fusion. Spinal fusion is a surgical technique where two or more vertebrae of the spinal column are fused together to eliminate the motion between the fused vertebrae. Spinal fusion is used to treat conditions where the spine exhibits instability. Spine instability may result from causes such as fracture, scoliosis and spondylolisthesis, where one or more vertebrae move in a forward direction relative to the other vertebrae. Spinal fusion with discectomy is also performed for herniations of the discs. This surgery involves removal of the affected disc and fusion of the adjacent vertebrae. Traditionally, bone grafts have been used to fuse the vertebrae, but various types of vertebral implants have also been used.

The use of bone plate and bone screw fixation systems for treating injuries to bones is well established. In most instances, a bone plate is positioned over and surrounding the bone injury area and secured to the bone. The bone plate is secured to the bone by bone screws or other similar fasteners inserted through holes in the bone plate and into the bone itself. The screws are tightened so that the bone plate holds the bone to be treated in place in order to insure proper healing. Early fixation devices tended to be applicable only to long bone injuries with only limited uses for lower lumbar spinal injuries and disorders. The use of plate/screw fixation systems later expanded, however, to include more uses for spinal injuries, including fusion of vertebrae including fixation devices for treating cervical vertebrae injuries. Notwithstanding the foregoing, there remains a need for improved methods and devices for treating spinal instability.

SUMMARY OF THE INVENTIONS

An implantable device for supporting bony structures comprises a spacer or plate element including at least one opening extending at least partially through the spacer or plate element. A helically-shaped element is configured to extend through the opening to secure the spacer or plate element to a bone.

In one arrangement, the opening in the space element includes a groove with a helical shape of corresponding diameter and pitch as the helically-shaped element In another arrangement, an interbody spacer system for the spine comprises a helically-shaped wire and an implant body having a hole through which the wire passes that is smaller in diameter than the outer diameter of the wire.

In certain arrangements, the helical shape of both the wire and a groove or indentation in the spacer can be correspondingly timed (e.g., having a rotational position about the axis of the helix) such that as the helically-shaped wire passes through the spacer, the sharp tip is the first portion of the wire to come in contact with the bony structures. In certain arrangements, the helically shaped element and groove are timed with respect to having a common rotational position about the axis of a helix The helically-shaped element may include a sharp tip capable of piercing the bone on one end and a feature that engages a driving instrument on the opposite end. In some arrangements, the sharp tip comes into contact with the bone from a generally perpendicular direction.

In some arrangements, the device may comprise a design feature that prevents the helical-shaped element from turning once it has reached its final desired implanted position.

In some arrangements, the device is configured such that the helically-shaped element extends through the opening to secure the spacer element to a superior vertebral body. The spacer element may have at least a second opening configured such that a second helically-shaped element extends through the second opening to secure the spacer element to an inferior vertebral body.

In some arrangements, the opening in the spacer implant further comprises a hole insert. The hole insert may have a groove with a corresponding diameter and pitch to the helically-shaped element.

Another arrangement, a method for treating a spine comprises inserting an interbody spacer between two vertebral bodies and inserting a corkscrew-shaped fixation device through an opening in the interbody spacer to secure the interbody spacer to a vertebral body. Some methods may further comprise engaging a proximal end of the corkscrew-shaped fixation device to a proximal feature of the opening in the interbody spacer. Other methods may further comprise inserting a second corkscrew-shaped fixation device through a second opening in the interbody spacer to secure the interbody spacer to a second, adjacent vertebral body.

In some arrangements, an interbody spacer system for the spine comprises a helically-shaped wire, a spacer, and a plate having at least one hole through which the wire passes to secure the plate to a vertebral body adjacent to the spacer. The hole through which the wire passes may in some instances be of corresponding diameter and pitch as the helically-shaped wire. In other instances, the hole through which the wire passes is smaller in diameter than the outer diameter of the helically shaped wire. The system may further comprise a hole insert in the plate hole. In some arrangements, the plate may be attached to the interbody spacer.

BRIEF DESCRIPTION OF THE DRAWINGS

The structure and method of using the invention will be better understood with the following detailed description of embodiments of the invention, along with the accompanying illustrations, in which:

FIG. 12A is a view of a helical fixation device with a protrusion proximally

FIG. 12B is a front perspective view of an interbody spacer with a groove for receiving helical spacer protrusion.

FIG. 12C is a view of a helical fixation device and cap for helical fixation device.

DETAILED DESCRIPTION OF THE PREFERRED EMBODIMENTS

Figure 1:
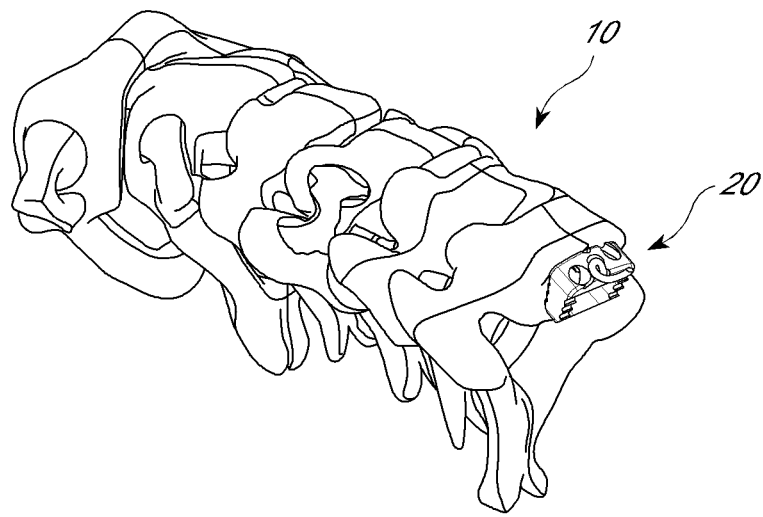
FIG. 1 is a view portion of the vertebral column with an interbody device positioned therein.
Figure 2A:
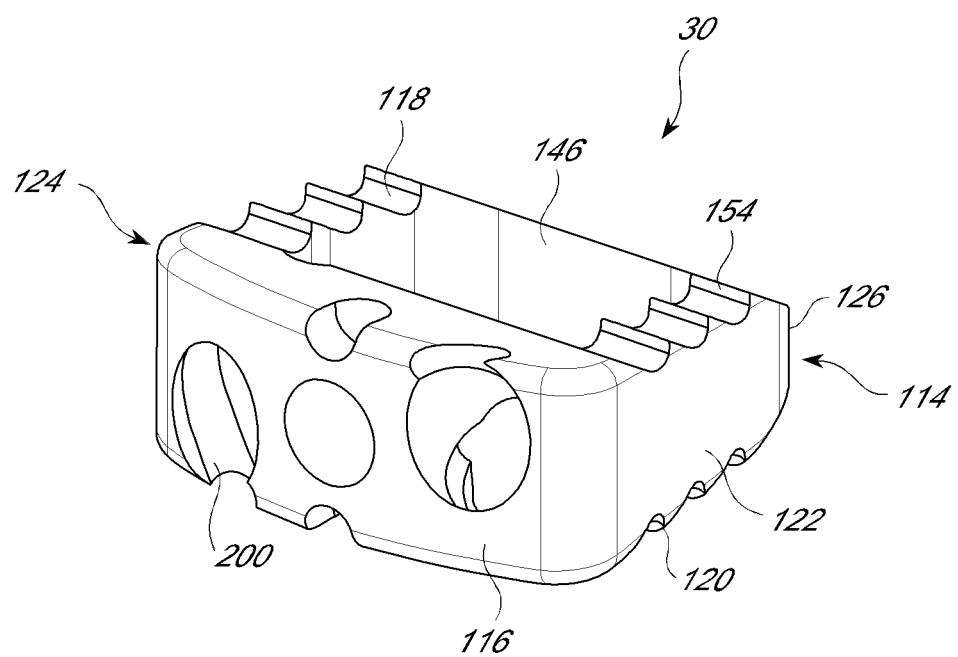
FIG. 2A is a front perspective view of a interbody spacer.
Figure 2B:
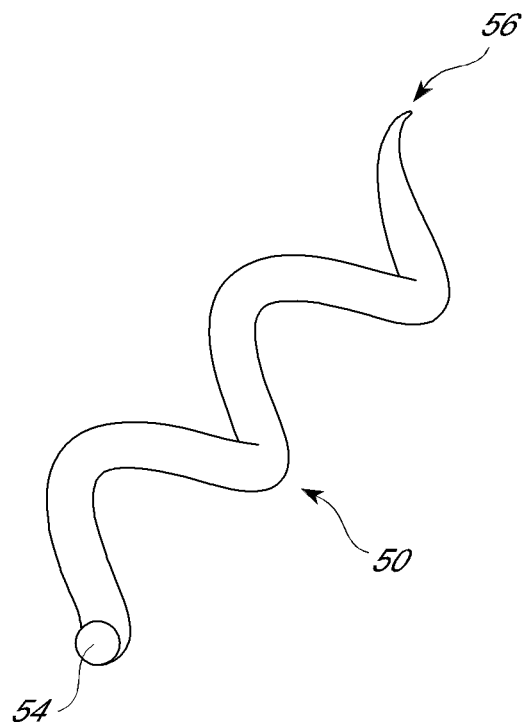
FIG. 2B is a view of an exemplary helical fixation device
Figure 2C:
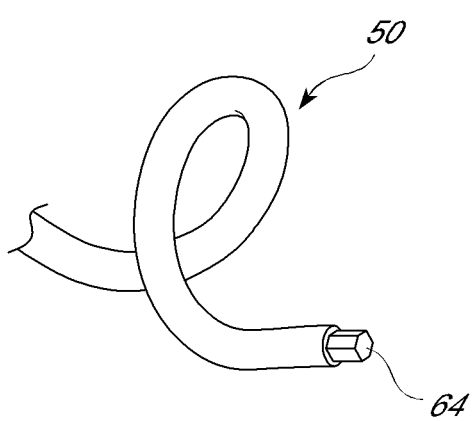
FIG. 2C is a view of the proximal segment of an exemplary helical fixation device.
Figure 2D:
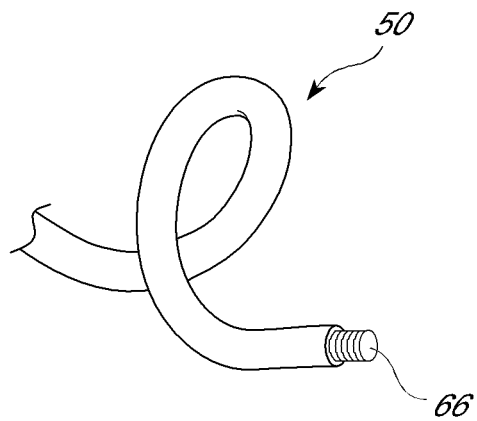
FIG. 2D is a view of the proximal segment of an exemplary helical fixation device.

The vertebral column 2 comprises a series of alternating vertebrae 4 and fibrous discs 6 that provide axial support and movement to the upper portions of the body. The vertebral column 2 typically comprises thirty-three vertebrae 4, with seven cervical (C1-C7), twelve thoracic (T1-T12), five lumbar (L1-15), five fused sacral (S1-S5) and four fused coccygeal vertebrae. FIG. 1 depicts a portion of the cervical spine with an embodiment of a interbody spacer system 20 positioned therein. The typical cervical vertebrae differ from the other vertebrae with relatively larger spinal canal, oval shaped vertebral bodies, bifid spinous processes and foramina in their transverse processes. These foramina transversaria contain the vertebral artery and vein. The first and second cervical vertebrae also further differentiated from the other vertebrae. The first cervical vertebra lacks a vertebral body and instead contains an anterior tubercle. Its superior articular facets articulate with the occipital condyles of the skull and are oriented in a roughly parasagittal plane. The cranium is able to slide forward and backwards on this vertebra. The second cervical vertebra contains an odontoid process, or dens, which projects superiorly from its body. It articulates with the anterior tubercle of the atlas, forming a pivot joint. Side to side movements of the head occur at this joint. The seventh cervical vertebra is sometimes considered atypical since it lacks a bifid spinous process.

In the figures and description herein, interbody spacer system 20 is shown positioned between the cervical vertebrae. However, it should be appreciated that in other arrangements the system 20 can be utilized in other portions of the spine.

Figure 3:
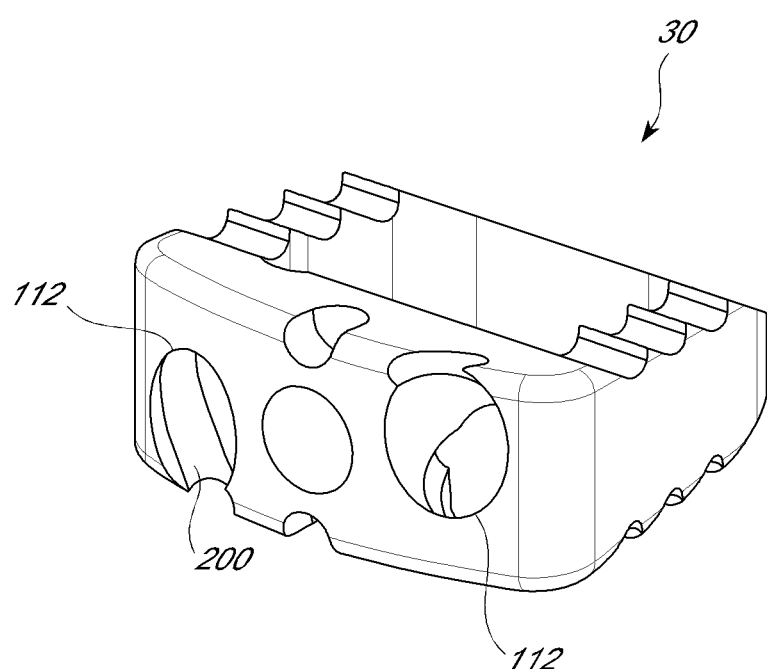
FIG. 3 is a front perspective view of a interbody spacer.
Figure 4:
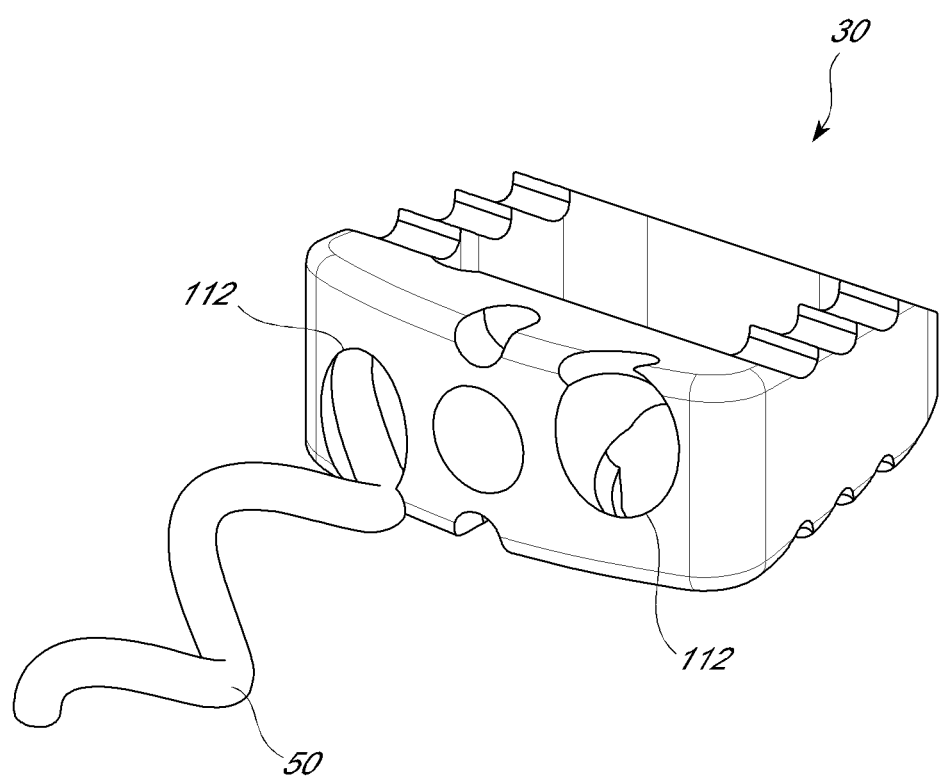
FIG. 4 is a front perspective view of a interbody spacer with a helical fixation device in a first position.
Figure 5:
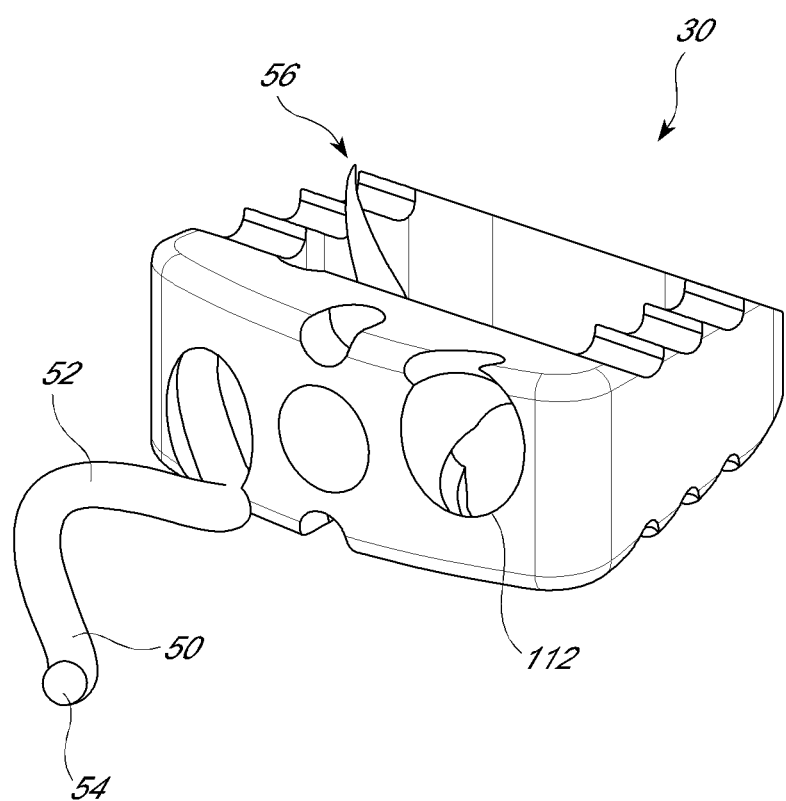
FIG. 5 is a front perspective view of a interbody spacer with a helical fixation device in a second position.
Figure 6:
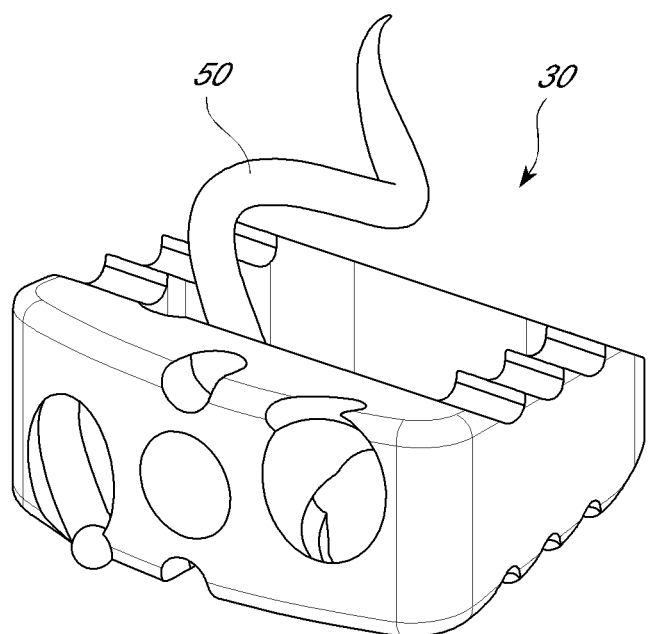
FIG. 6 is a front perspective view of a interbody spacer with a helical fixation device in a third position.
Figure 7:
FIG. 7 is a front perspective view of a interbody spacer positioned between vertebral bodies with a helical fixation device in a first position.
Figure 8:
FIG. 8 is a front perspective view of a interbody spacer positioned between vertebral bodies with a helical fixation device in a second position
Figure 9:
FIG. 9 is a side perspective view of a interbody spacer positioned between vertebral bodies with a helical fixation device in a first position.
Figure 10:
FIG. 10 is a front perspective view of a interbody spacer positioned between vertebral bodies with a helical fixation device in a second position.
Figure 11:
FIG. 11 is a front perspective view of a interbody spacer positioned between vertebral bodies with a helical fixation device in a third position.

The interbody system 20 comprises an interbody spacer or body 30 shown in FIGS. 2 and 3. The interbody spacer 30 can comprise any structure configured to maintain a separation and resist compression between two adjacent vertebral bodies. The spacer can have any of a variety of overall shapes, including but not limited to a rectangular box, a trapezoidal box, H-shaped, O-shaped, V-shaped, with or without one or more lumens within the spacing structure. As shown in FIGS. 2 and 3, the spacer 30 comprises a body 114 that can have an anterior surface 116, a superior surface 118 and an inferior surface 120, and side surfaces 122, 124, and a posterior surface 126. Each surface 116, 118, 120, 122, 124, 126 need not be flat, and can be curved or undulating or any combination thereof. The upper and lower surfaces 118, 120 can be configured for facing the superior and inferior vertebral bodies adjacent to an implantation site. The relative configuration of the upper surface 118 and lower surface 120 can vary, depending upon the relative position desired between the two adjacent vertebrae, the anatomical shape of the vertebrae, ease of insertion of the implant and other factors. For example, if a neutral vertical alignment is desired between two vertebrae, the upper and lower surfaces 118, 120 can have generally parallel planar orientations. If a non-neutral alignment is desired, for instance to maintain a natural spinal curvature in the cervical region, the upper and lower surfaces 118, 120 can have a wedge-like relationship to allow fixation of the vertebrae in the desired non-neutral position. A non-neutral alignment with respect to the anterior-posterior direction can also be used to compensate for excessive lordosis or kyphosis in other portions of the vertebral column. The height of the body 114 at any section between the upper and lower surfaces 118, 120 can be further configured to accommodate degenerative changes or anatomical anomalies to provide fixation in the desired relative position. Likewise, the side surfaces 122, 124 of the spacing structure 114 can be generally parallel or skewed. In some embodiments, the side surfaces 122, 124 of the implant 30 taper with increasing distance from the anterior side 116 of the implant 100. A tapered spacing structure can facilitate insertion of the implant 30 into the intervertebral space. In other embodiments, the one or more side surfaces can flare distally or have both tapering and flaring portions.

FIGS. 2 and 3 illustrate an embodiment comprising a spacer 30 with windows or holes 146 between the outer surfaces. These windows or holes can allow bony growth into the windows or holes. The space 146 within and/or between the posterior members can also be filled with graft materials (not shown). The graft material can be an autograft, allograft, xenograft or synthetic material. Synthetic graft material can be ceramic-based, silicon-based or calcium-based. The graft material can also include osteoinductive factors to promote bone ingrowth. One skilled in the art will appreciate that there are many varieties of synthetic graft materials and constituents that can be used between or about the hyoid bone segments.

One or more surfaces of the implant can also have surface projections, indentations, or holes or pores that can further alter the characteristics of the implant. Referring to FIGS. 2 and 3, in some embodiments, angled projections, barbs, teeth 154 or ramped surfaces can incline outwardly from one or more spacer surfaces and can be provided on one or more surfaces that allow insertion of the spacing structure in one direction but resist movement in the opposite direction. These teeth 154 can be advantageous in reducing the migration of the device out of the intervertebral space. Improved fixation of the spacer 30 can maintain device position during initial placement between vertebral bodies, and can also reduce the forces acting upon the screws or other retaining structures (described below), thereby reducing the risk of backout. The teeth 154 are preferably provided on the superior and/or inferior surfaces 118, 120 of the spacer 30, but other surfaces can also have teeth or other tissue engagement structures.

In some embodiments, the tissue engagement structures can be combined with indentations, holes or pores for allowing bony ingrowth or filling with bony matrix or graft materials as previously described. These holes can be utilized with other surface features to further enhance insertion and stabilization of the implant.

In some embodiments, the spacer can have a height of about 4 mm to about 50 mm, or preferably about 4 mm to about 12 mm. In some embodiments, the spacer can have a height of about 6 mm to about 9 mm. In some embodiments, the spacer can have a length as measured from the bone facing surface of the fixation plate to the most posterior end of the spacer of about 5 mm to about 25 mm. In some embodiments, the spacer length can be about 10 mm to about 15 mm. The width of the spacer can be generally about 5 mm to about 25 mm, and in some situations, about 10 mm to about 15 mm. One skilled in the art can dimension the spacer based upon the implantation location and specific vertebral morphology, neurological anatomy and disease state.

The spinal fusion implant can include, be made of, treated, coated, filled, used in combination with, or contain artificial or naturally occurring materials suitable for implantation in the human spine. These materials can include any source of osteogenesis, bone growth-promoting materials, bone derived substances, bone morphogenetic proteins, hydroxyapatite, genes coding for the production of bone, and bone including, but not limited to, cortical bone. The implant can also be formed of material such as metal including, but not limited to, titanium and its alloys, surgical grade plastics, plastic composites, ceramics, or other materials suitable for use as a spinal fusion implant. In some embodiments, the device can comprise a radiolucent material, a radio-opaque material, or a combination thereof. A device that is partially or completely radiolucent can be advantageous when evaluating the effect of the implant post-implantation. Many existing spinal fixation plates and/or spacers obscure visualization of the vertebrae, which can complicate post-operative treatment, diagnosis and prognosis of the patient's condition. The implant can include at least in part materials that are bioabsorbable in the body. The implant of the described embodiments can be formed of a porous material or can be formed of a material that intrinsically participates in the growth of bone from one of adjacent vertebral bodies to the other of adjacent vertebral bodies. The implant can be treated with, coated with, or used in combination with substances to inhibit scar tissue formation. The implant of the described embodiments can be modified, or used in combination with materials to provide antibacterial properties, such as, but not limited to, electroplating or plasma spraying with silver ions or other substance. The implant can optionally comprise an electrical source to provide ionophoresis of the silver ions into the surrounding tissue to prevent infection. The antibacterial properties can include bactericidal and/or bacteriostatic characteristics. Similarly, anti-fungal characteristics can also be provided. Any of these materials as appropriate can be used at any time after the implant(s) are inserted.

To secure the spacer 30 between vertebral bodies, the system 20 can include a fixation device 50 shown in FIGS. 4-11. In the illustrated embodiment, the fixation device 50 can comprise a helical and/or corkscrew shaped body 52 or wire with a proximal end 54 and a distal end 56. See FIG. 5. The distal end 56 can be formed into a sharp tip that can be configured to penetrate bone (e.g., the endplates of the vertebral body). The proximal end 54 can be configured to engage a driving instrument. For example, as in FIGS. 2C-D, the proximal end may have a portion with hexagonal shape, protruding slot, or threading to engage corresponding hex-headed or threaded driver. Alternatively, the proximal end of the fixation device may have central bore with female threads, internal hex, or any other method of removably coupling to a driver. In some embodiments, the fixation device 50 can be formed of a metal such as, for example, titanium or titanium alloy. The device 50 can be formed in a variety of ways, such as, for example by bending a straight wire or rod into a helical or corkscrew arrangement. In other embodiments, the device 50 can be machined or otherwise formed into the illustrated arrangement. In some embodiments, the device 50 may be made of PEEK or other radiolucent material.

Referring to FIGS. 2-11, the spacer 30 can have one or more spaces or holes 112 extending from the anterior surface 116 of the spacer 30. The holes 112 are configured to accept the fixation device 50 described and/or other attachment elements for anchoring the body 30 to the vertebral bone. In the illustrated embodiment, one screw hole 112 is slanted or orientated such that the opening is directed towards the superior vertebral body and the other hole 112 is slanted or orientated such that the opening is directed towards the inferior superior body.

In the illustrated arrangement, the hole 112 includes a groove 200. The groove 200 can be configured to have the same or similar helical shape (e.g., corresponding diameter and pitch) as the fixation device 50. In this manner, in one arrangement, the helical shape of both the fixation device 50 and the groove 200 can being correspondingly timed (e.g., having a rotational position about the axis of the helix) such that as the helically-shaped device 50 passes through the body 30, the sharp tip is the first portion of the fixation device 50 to come in contact with the bony structures. See e.g., FIG. 10. The tip 56 may come into contact with the bony structure generally perpendicular to the bony surface. This arrangement advantageously inhibits the fixation device 50 from being deflected away from the vertebral body as it is inserted into the bone. In other embodiments, the body 30 can be formed without the groove. The spacer 30 and/or the fixation device 50 can include a design feature that prevents the fixation device 50 from turning once it has reached its final desired implanted position. For example, in one arrangement, as shown in FIGS. 12A-B, the proximal end 54 of the fixation device 50 and the body 30 can have interlocking shapes 254, 256 that interlock to limit rotation of the fixation device once it has reached its fully inserted position. For example, a protrusion from the fixation device may interlock with a corresponding groove or slot in the body at the entrance to the hole. Alternatively, in another arrangement, shown in FIG. 12C, a supplemental component 72 such as a cap may be coupled a complementary surface of the proximal end of the helical fixation device 66 or body 30 to cover or limit rotation of the fixation device (e.g. by providing interference to rotation). This may couple to the fixation device or body through threads, friction fit, or any other coupling mechanism. The cap may have a central stem with male threading to engage central bore in the proximal end of the fixation device. There may be corresponding groove in the body for receiving the supplemental component or the supplemental component may block further insertion.

In other arrangements, the hole 112 in the spacer may have a diameter which is smaller than the outer diameter of the helix. In some arrangements, the hole has a groove 200 which is smaller than the outer diameter of the helix and has a correspondingly larger pitch than that of the helix. In other arrangements, there is no groove.

Figure 13:
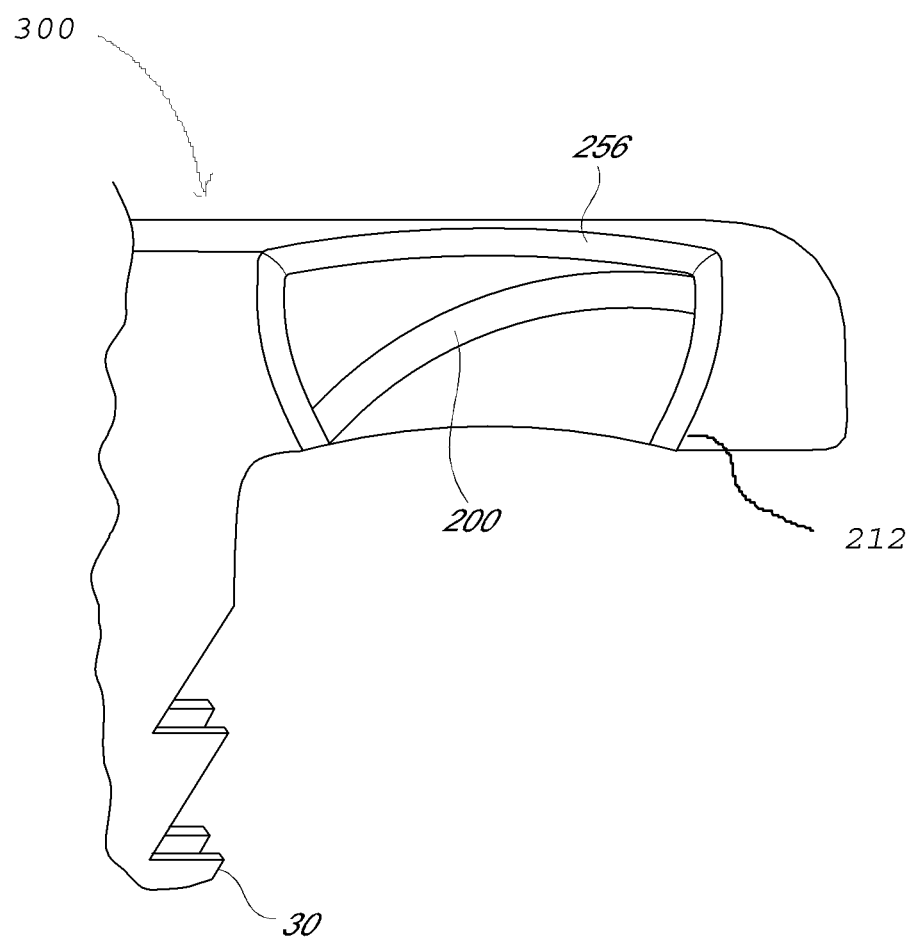
FIG. 13 is a view of a portion of a spacer system with hole insert for helical fixation device.

In some arrangements, as shown in FIG. 13, the hole 212 in the system 300 may have a hole insert 256 through some or all of the opening in the plate or spacer. The hole insert 256 provides an intermediate layer of material between the helical fixation device and the inner surface of the flange hole 200. The hole insert 256 may comprise a generally polymer, metallic, or ceramic member comprising an outer flange hole contacting surface and an inner fixation device contacting surface, where the outer flange hole contacting surface is shaped to conform to at least a portion about the inner surface of the flange hole 112. The hole insert may have a helical groove 200 on the inner fixation device contacting surface corresponding to the pitch and diameter of the helical element. In one embodiment of the invention, the flange hole insert 256 is capable of absorbing wear forces transmitted between the system 300 and the helical fixation element. The hole insert 256 may comprise a material complementary to the material used in the helical element, to reduce wear. Absorption of the forces between these two components of the implant may reduce the risk of implant failure and/or loosening that occurs at the interface between the two components.

In one preferred embodiment, the flanged interbody device comprises a polyaryl polymer, including but not limited to PEK, PEEK, PEKK, PEKEKK or a blend thereof, and the insert comprises a titanium or titanium alloy. Other combinations may also be used as is known by those with skill in the art.

Figure 15:
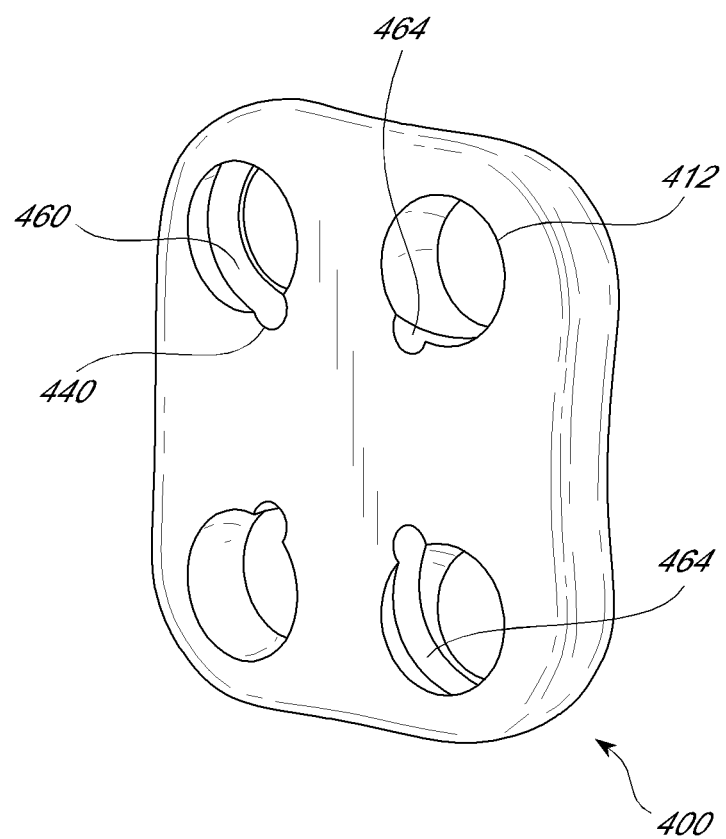
FIG. 15 is a view of a plate for use with one or more helical fixation devices.

While a flanged interbody fusion device 300 is shown in FIG. 13, hole inserts may likewise be used in openings in an interbody spacer 30 such as those shown in FIGS. 1-11 or in a plate 400 such as that shown in FIG. 15.

The fixation device 50 described has certain advantages over traditional fixation screws used with interbody spaces. For example, as compared to screws, a screw hole does not need to be prepared. Accordingly, the procedure can be faster. In addition, less bone is removed from the vertebral body. The fixation device 50 can also have increased pull out strength as compared to screws.

Figure 14:
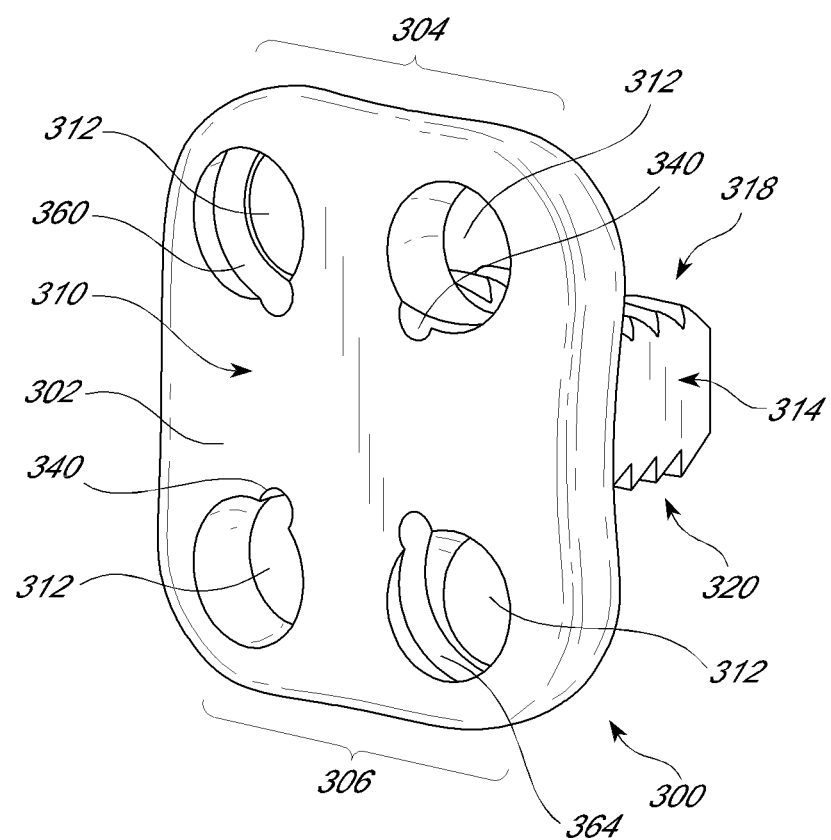
FIG. 14 is a view of a flanged fusion device for use with one or more helical fixation devices.

It should be appreciated that while the fixation device 50 is shown with an interbody spacer in other embodiments the fixation device can be used with other spinal fixation devices, such as, for example, a flanged interbody devices and various plates (e.g., cervical plates). In one embodiment of the invention, an interbody vertebral implant 300 is provided. As shown in FIG. 14, in one embodiment the implant 300 comprises a stabilization or fixation plate 302 having an upper portion 304 and a lower portion 306, and a bone facing surface 308 and an access surface 310. In use, typically the bone facing surface 308 will actually contact the vertebral bone surface, but in other embodiments, other structures or components may lie in between the bone facing surface 308 and the bone surface of the vertebra. Each upper portion 304 and lower portion 306 has one or more spaces or holes 312 oriented between the bone facing surface 308 and the access surface 310 that are configured to accept helical or corkscrew shaped fixation devices for anchoring the implant 300 to the vertebral bone. One or more spacers or spacing structures 314 are located on the bone facing surface 308 of the fixation plate 302. The spacers 314 are typically integrated with the fixation plate 302 about the bone facing surface 308. The upper and lower surfaces 318, 320 are configured for facing the superior and inferior vertebral bodies adjacent to an implantation site. The relative configuration of the upper surface 318 and lower surface 320 may vary, depending upon the relative position desired between the two adjacent vertebrae, the anatomical shape of the vertebrae, ease of insertion of the implant and other factors.

The holes 312 in the flange component may contain a groove 360,364 configured to accept a helical fixation structure with corresponding pitch and diameter or with slightly larger diameter. The grooves 360 may be configured to accept a helical fixation device with clockwise rotating helix or counterclockwise rotating helix 364. The hole may have a groove 340 at the interface with the proximal surface of the plate to direct initial placement of the helical fixation device, to engage with a corresponding feature in the helical fixation device to maintain its final position, or both.

In FIG. 15, a plate 400 for spinal fixation is shown with holes 412 configured to accept a helical fixation element. The grooves 460 may be configured to match a helical fixation structure in which the turns of the helix are configured in a clockwise fashion. Alternatively, some or all other grooves 464 may match a helical fixation structure configured with counter-clockwise turns. This may advantageously affect the pull out strength of the construct. Notches or grooves 440 in the plate may interfit with the proximal end of the helical structure as well as provide the starting point for the tip of the helical fixation structure such that the tip will contact the bone at an appropriate angle.

In some embodiments, the patient can be intubated and general anesthesia can be achieved. The patient can be prepped and draped in the usual sterile fashion. An anterior approach to the spine can be used to expose the anterior vertebral bodies. Many anterior approaches to the vertebral column are described in various medical texts such as Campbell's Operative Orthopaedics, 10th ed., edited by Canale et al., pp. 1569-1588, herein incorporated by reference. In some embodiments, the upper cervical spine can be accessed. The anterior upper cervical spine can be accessed by a transoral or retropharyngeal route, or by using a subtotal or extended maxillotomy. In other embodiments, the lower cervical spine, cervicothoracic junction, thoracic spine, thoracolumbar junction, lumbar region, lumbosacral junction, sacrum or combination of the above regions can be accessed.

The intervertebral space can be debrided. In some embodiments, a flanged interbody implant can be packed with natural or artificial bone matrix and/or other osteogenesis factors and inserted into the intervertebral space. The flange can be positioned against the anterior cervical vertebral bodies and attached with one or more helically shaped wires. In other embodiments, an interbody spacer may be inserted into the intervertebral space and attached to a superior vertebral body, an inferior vertebral body, or both with one or more helically shaped structures. Pilot hole in the vertebral body cortex may be prepared for the one or more helically shaped structures using a punch. The helically shaped structures may be removably coupled to an inserter for their insertion. The inserter may comprise a handle, and may advance the helically shaped structure by, for example, rotation or impaction of the handle. The operative site can be irrigated with antibiotics and the operative field can be sutured closed. The vertebral column can be accessed and one or more intervertebral spaces can be identified and accessed. In some embodiments, two or more intervertebral spaces can be accessed, and in still other embodiments, two or more adjacent intervertebral spaces can be accessed. The operative site can be rinsed with antibiotic solution and the operative field can be closed in layers.

Although the present invention has been described in relation to various exemplary embodiments, various additional embodiments and alterations to the described embodiments are contemplated within the scope of the invention. Thus, no part of the foregoing description should be interpreted to limit the scope of the invention as set forth in the following claims. For all of the embodiments described above, the steps of the methods need not be performed sequentially.

What is claimed is:

1. A method for treating a spine, comprising:
    inserting an interbody spacer between two vertebral bodies;
    engaging a distal tip of a helically-shaped wire with a notch at an interface with a hole of a plate, wherein the notch extends a helically shaped groove to a proximal surface of the plate, the notch and the helically shaped groove directly formed in the plate; and
    engaging the helically-shaped wire with the helically shaped groove and into a vertebral body adjacent to the interbody spacer, wherein the notch directs the initial placement of the distal tip of the helically-shaped wire into the vertebral body.

2. The method of claim 1, further comprising maintaining a fully inserted position of the helically-shaped wire in the vertebral body.

3. The method of claim 1, further comprising limiting further rotation of the helically-shaped wire.

4. The method of claim 1, further comprising limiting further insertion of the helically-shaped wire.

5. The method of claim 1, further comprising limiting further movement of the helically-shaped wire.

6. The method of claim 1, further comprising engaging a feature of the helically-shaped wire with the notch.

7. The method of claim 1, wherein the helically shaped groove comprises a rounded inner surface.

8. The method of claim 1, wherein the helically shaped groove and the helically-shaped wire each comprises coils which are spaced the same distance apart.

9. The method of claim 1, further comprising engaging a second helically-shaped wire with a second helically shaped groove of the plate.

10. The method of claim 1, wherein the helically-shaped wire comprises clockwise turns.

11. A method for treating a spine, comprising:
    inserting at least a portion of an implant between two vertebral bodies;
    engaging a distal tip of a helically-shaped fixation device with a notch at an interface with a proximal surface of the implant, wherein the notch provides a rotational starting point for the distal tip; and
    engaging the distal tip of the helically-shaped fixation device with a helical groove directly formed in the implant, wherein the helical groove provides a rotational ending point for the distal tip such that the distal tip contacts a vertebral body at a pre-determined angle.

12. The method of claim 11, further comprising maintaining a fully inserted position of the helically-shaped fixation device in the vertebral body.

13. The method of claim 11, further comprising limiting further rotation of the helically-shaped fixation device.

14. The method of claim 11, further comprising limiting further insertion of the helically-shaped fixation device.

15. The method of claim 11, further comprising limiting further movement of the helically-shaped fixation device.

16. The method of claim 11, wherein the helically-shaped fixation device comprises spaced apart adjacent coils.

17. The method of claim 11, wherein the helical groove comprises a linear axis through the implant.

18. The method of claim 11, wherein the distal tip comes into contact with the vertebral body from a perpendicular direction.

19. The method of claim 11, wherein the helical groove comprises a semi-circular inner surface.

20. The method of claim 11, further comprising engaging a second helically-shaped fixation device with a second helical groove of the implant.

* * * * *